United States Patent [19]

Miyake et al.

[11] Patent Number: 5,003,611
[45] Date of Patent: Mar. 26, 1991

[54] METHOD FOR DETECTION OF THE PRESENCE OF UNDESIRED MICROORGANISMS

[75] Inventors: Shinichi Miyake; Fumihiko Yonemori; Masayuki Kometani, all of Osaka, Japan

[73] Assignee: Sumitomo Electric Industries, Ltd., Osaka, Japan

[21] Appl. No.: 226,775

[22] Filed: Aug. 1, 1988

[30] Foreign Application Priority Data

Jul. 31, 1987 [JP] Japan ............................... 62-192023

[51] Int. Cl.$^5$ .............................................. G06K 9/36
[52] U.S. Cl. .......................................... 382/6; 382/18; 356/435
[58] Field of Search ................... 382/6, 18, 19, 28, 31; 356/432, 435; 250/259; 358/107; 377/6

[56] References Cited

U.S. PATENT DOCUMENTS

| | | | |
|---|---|---|---|
| 3,773,426 | 11/1973 | Mudd | 356/435 |
| 4,519,087 | 5/1985 | Dein Doerfer | 382/6 |
| 4,564,444 | 1/1986 | Hiroaoka et al. | 382/6 |
| 4,794,450 | 12/1988 | Saito et al. | 382/6 |
| 4,856,073 | 8/1989 | Farber et al. | 382/6 |

FOREIGN PATENT DOCUMENTS

| | | |
|---|---|---|
| 0189599 | 12/1985 | European Pat. Off. |
| 60-210997 | 4/1984 | Japan |
| 61-152282 | 12/1984 | Japan |
| 62-115297 | 11/1985 | Japan |

*Primary Examiner*—David K. Moore
*Assistant Examiner*—Yon Jung
*Attorney, Agent, or Firm*—Cushman, Darby & Cushman

[57] ABSTRACT

A method of detecting undesired microorganisms when cells are cultured in a light permeable container is disclosed. TV camera monitors the image of a well containing microorganisms through a microscope. The output of the TV camera is processed by a picture digital processor so as to count the number of cultured living cells. On the other hand, change of the light absorption of the visible light by the cultured solution is measured. Then the number of undesired microorganisms can be calculated by the number of the living cells and change of the light absorption.

10 Claims, 4 Drawing Sheets

METHOD FOR DETECTION OF THE PRESENCE OF UNDESIRED MICROORGANISMS

FIELD OF THE INVENTION

The present invention relates to a method for detecting undesired microorganisms contaminating a cell culture, which method permits early discovery of microorganisms which have invaded the culture and prevention of the growth of microorganisms in the culture.

DESCRIPTION OF THE PRIOR ART

A cell culture which contains a lot of nutritive substances is susceptible to contamination by undesired microorganisms floating in the air, such as incomplete bacteria and gram negative aerobic bacilli, especially when an exchange of a culture medium or an examination of the growth rate of the desired cells is conducted in the course of cultivation. The microorganisms invading the cell culture usually grow faster than the desired cells. Accordingly, it is often observed that the microorganisms which invade one well on a multiwell microplate spread to other wells, and it is not rare that all plates in an incubator are contaminated with undesired microorganisms.

It is necessary, therefore, to examine the presence or absence of contamination of the cell culture by microorganisms as early as possible so that the contaminated well or plate may be sterilized or discarded to prevent the microorganisms from further spreading.

The contamination by microorganisms has long been visually examined using a microscope. However, such measure necessitates worker's manipulation and also gives additional chance of contamination by undesired microorganisms. In addition, the visual examination is not satisfactory in terms of accuracy or reliability on the detection of the microorganisms and also takes considerable time. Furthermore, the visual examination has an additional drawback, especially when a lot of microplates have to be examined, that the activity of the cultured cell tends to decline during the long-term exposure to outer-culturing atmosphere which is necessary for the examination.

SUMMARY OF THE INVENTION

An essential object of the present invention is to provide a method of detection of undesired microorganisms in the cell culturing device which is able to detect the undesired microorganisms automatically and rapidly with a highly accurate measurement result.

According to the present invention, there is provided a method of detecting undesired microorganisms when cells are cultured in a light permeable container, characterized by counting the number of cultured living cells appearing in a digital cultured cell picture which is obtained by a picture processing device for processing picture signals fed from a television camera coupled to an observation means provided for observing the container and the change of the absorption of the visible light by the cultured solution.

According to the present invention, presence of the undesired microorganisms can be detected when the number of the living cells is small but the absorption of the visible light is increased compared to the absorption measured in a previous measurement. It is desired that the visible light is light of a wave length is not absorbed by an indicator contained in the culture solution.

According to another feature of the present invention, presence of the undesired microorganisms can be detected when the number of cultured cells are small and the pH value of the culture solution is greatly decreased compared to the previous pH measurement value. It is desired to calculate the pH value by change of the absorption of the visible light.

It is desired that the change of light absorption includes more than two kinds of light including a first light having a wave length which is absorbed by the indicator contained in the culture solution and the a second light of wave length which is not absorbed by the indicator. It is further desired that at least one of the changes of light absorption is for detecting the change of pH value and is due to the absorption change by phenol red contained in the culture solution.

According to one feature of the present invention, the picture data taken in a picture processing device is processed and the number of cultured living cells is measured by a computer. In addition, the change of the visible light absorption by the culture solution is measured or pH value of the culture solution is indirectly measured by the visible light absorption using an indicator. The presence of the undesired microorganism can be detected based on the measured values in a semiquantitaive determination.

According to the present invention, the presence of the undesired microorganisms can be detected when the measured value of the living cells is small and the absorption of the visible light by the culture solution is greater than the absorption measured in the previous measurement or when the measured value of the living cells is small and pH value of the culture solution is greatly decreased compared to the pH value measured in the previous measurement.

In cases where the cells have not yet cultured, the number of living cells is small. In this condition, as the way of measuring of the number of the living cells, there may be employed a method that uses the difference of the brightness which is a property of the living cells or another method of performing a process using a spatial filter or matched filter as shown in the Japanese patent publication No. 60-256154.

Under such a condition that the living cells are scarcely present, since the visible light of a wave length which is not absorbed by the indicator contained in the culture solution is decreased in a light permeability only by the absorption and scattering by the dead cells and the micro plates, the light absorption is small. If the undesired organisms are mixed and grow under the condition mentioned above, the absorption and scattering of light by the undesired organisms increase despite the fact that the measured number of the cultured living cells is small. As the result, when the measured number of the living cells is small and the change of the absorption of the visible light is largely greater than the light absorption measured in the last measurement period in the past, the presence of the undesired organisms can be detected.

According to the method of the present invention, the presence of the undesired microorganisms can be detected by measuring the light absorption using not only light of a wave length which is not absorbed by the indicator contained in the culture solution but also light of a wave length which is absorbable in the indicator. Besides, the light absorption by the indicator contained in the culture solution may change due to the change of pH value of the culture solution. Accordingly, the latter method of detecting the presence of the undesired microorganisms using the light of the wave length which is absorbable by the indicator possesses a problem. Therefore, according to the present invention, pH is measured without contacting the culture solution. As the method of detecting the pH value without contacting the culture solution, it is desired to detect the change of the light absorption by the indicator such as phenol red contained in the culture solution for calculations the pH value.

In order to detect the change of pH value, phenol red with a low concentration that does not harm the cells is contained in the culture solution. With the phenol red with such low concentration, it is possible to detect the pH value of the culture solution by using any one or both of light absorption peaks at 430 to 440 nm (nano meter) wave lengths and at 560 nm.

In order to calculate the pH value accurately, it is necessary to calculate the pH value excluding either the light absorption and scattering due to the stain of the container such as a microplate, a dish and a culture bottle and the light absorption and scattering due to the living cells and dead cells existing in the container. For this purpose, it is desired to calculate the pH value by subtracting the light absorption at the wave length of 650 nm from the light absorptions at the wave length of 430 to 440 nm and the wave length of 560 nm taking a ratio thereof. According to this method, it is possible to calculate an accurate pH value eliminating the undesired effects of the light absorption and scattering other than the change of pH value.

As mentioned above, according to the method of the present invention, it is possible to detect automatically the invasion of the undesired microorganisms in a very short time with a high accuracy compared to the conventional manually visual measurement using a microscope.

DETAILED DESCRIPTION OF THE PREFERRED EMBODIMENT

Figure 1:
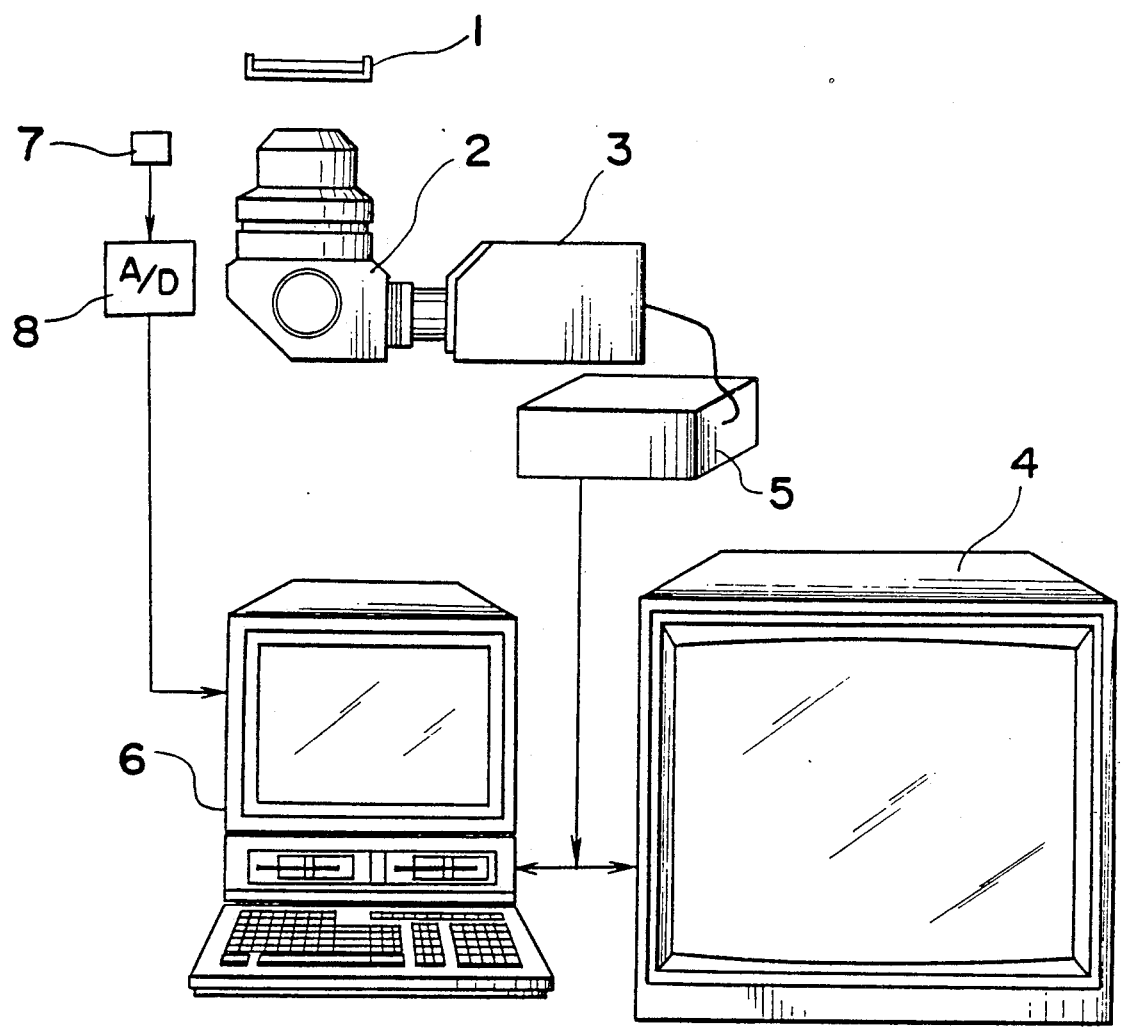
FIG. 1 is a schematic diagram showing an embodiment of a system for detecting undesired microorganisms according to the present invention.
Figures 2, 3:
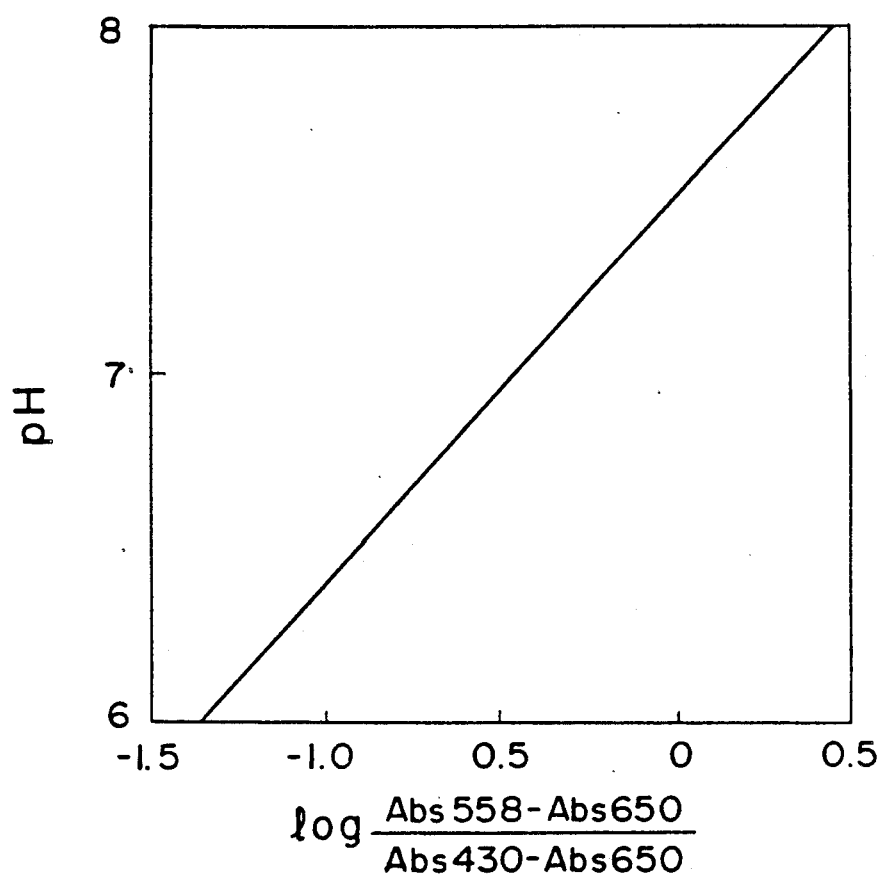
FIG. 2 is a schematic diagram showing an example of a spatial filter used in the system shown in FIG. 1.
FIG. 3 is a graph showing relations between the change of light absorption in the sample and pH value.
Figure 4:
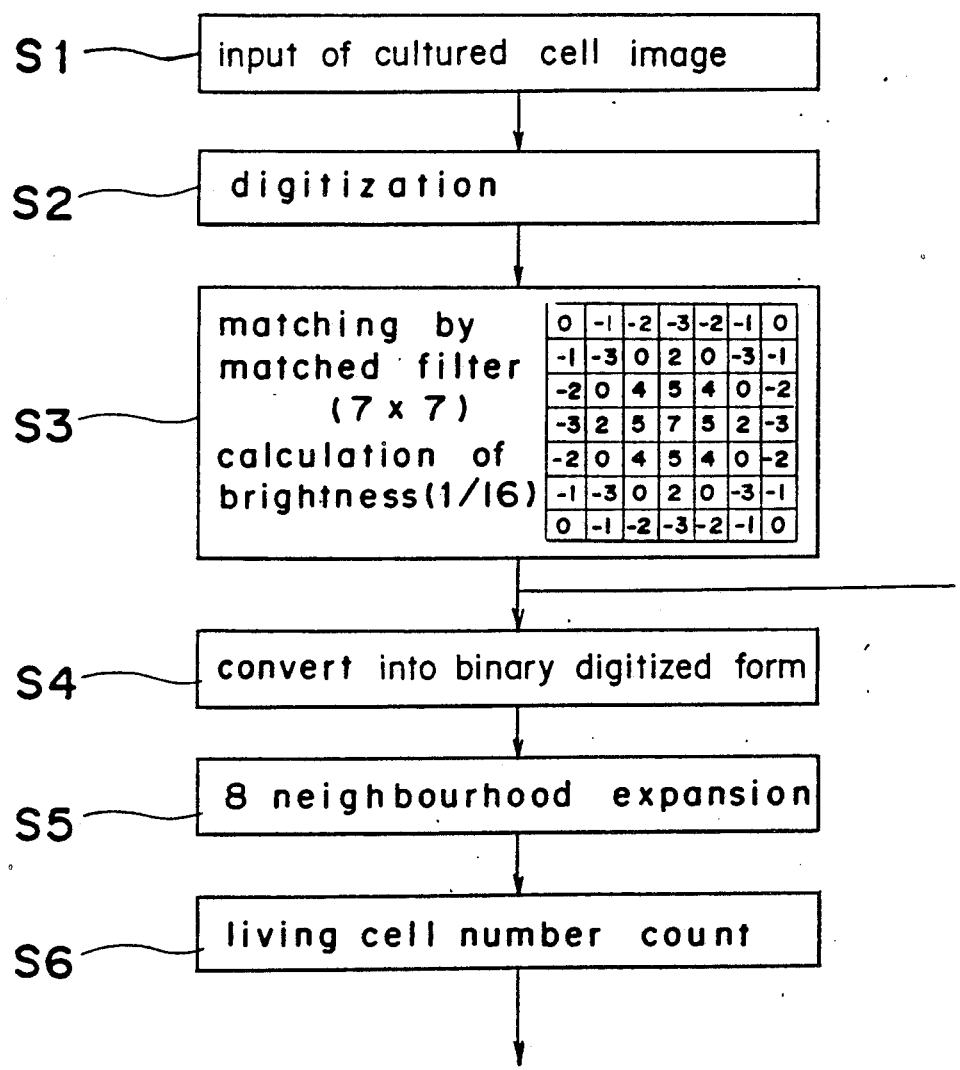
FIGS. 4 and 5 are flow charts showing essential parts of the operation of the system shown in FIG. 1.

Referring to FIG. 1, there is provided a microscope 2 to observe a well 1 of a microplate having 96 wells (referred to as a 96 well plate hereinafter) from below. Each of the wells is light permeable so that the microscope can view the entire area of the bottom of the well 1 and to view the contents contained in the well 1. The microscope 2 is coupled to a CCD camera 3 for generating electric signals representing the image viewed by the microscope for every pixels of CCD camera in a known manner. The CCD camera 3 is coupled to a image processing device 5 the output of which is coupled to a computer 6 and a monitor television 4. The image signal processor 5 digitize the image signals of the CCD camera 3 and processes the image signals to produce the data showing the living cells in the well 1 by using a matched filter. An example of the matched filter is shown in FIG. 2. The process of generating the data representing the living cells is shown in a flow chart shown in FIG. 4. In the step S1 the image signals from the CCD camera 3 are taken in the image processing device 5. The image signals are digitized and stored in a memory (not shown) in the step S2. The digital image signals contained in 7×7 picture cells are subjected to a matching process using the matched filter or spatial filter for a convolution processing in a known manner. This process is generally expressed by the following equation.

$$A'x,y = \frac{1}{C1} \sum_{i=-N}^{+N} \sum_{j=-N}^{+N} A_{x+i,y+j} \times f(i,j)$$

wherein

Ax,y: digital brightness at x and y position of the input image

A'x,y: digital brightness at x and y position after filtering f(i,j): coefficient corresponding to each pixel of the filer C1: coefficient The image data passed or matched with the matched filter in the step S3 which representing the culture cell is compared with a threshold value T1 in terms of the brightness of the cell for selecting the living cell so that Ax, y is converted into Bx, y of a binary digitized form (Bx, y=1 or 0). Then *8 neighbor expansion process is performed for each picture cell in the step S5.

Then the number of the living cells is calculated in the step S6 using the following equation.

$$\text{Number of the living cells} = \frac{1}{C_2} \sum_{x,y} Bx,y$$

C2: The number of the pixels which one living cell occupies

C2: The number of the pixels which one living cell occupies.

The above mentioned processing is performed in the image processor 5 and computer 6.

Figure 5:
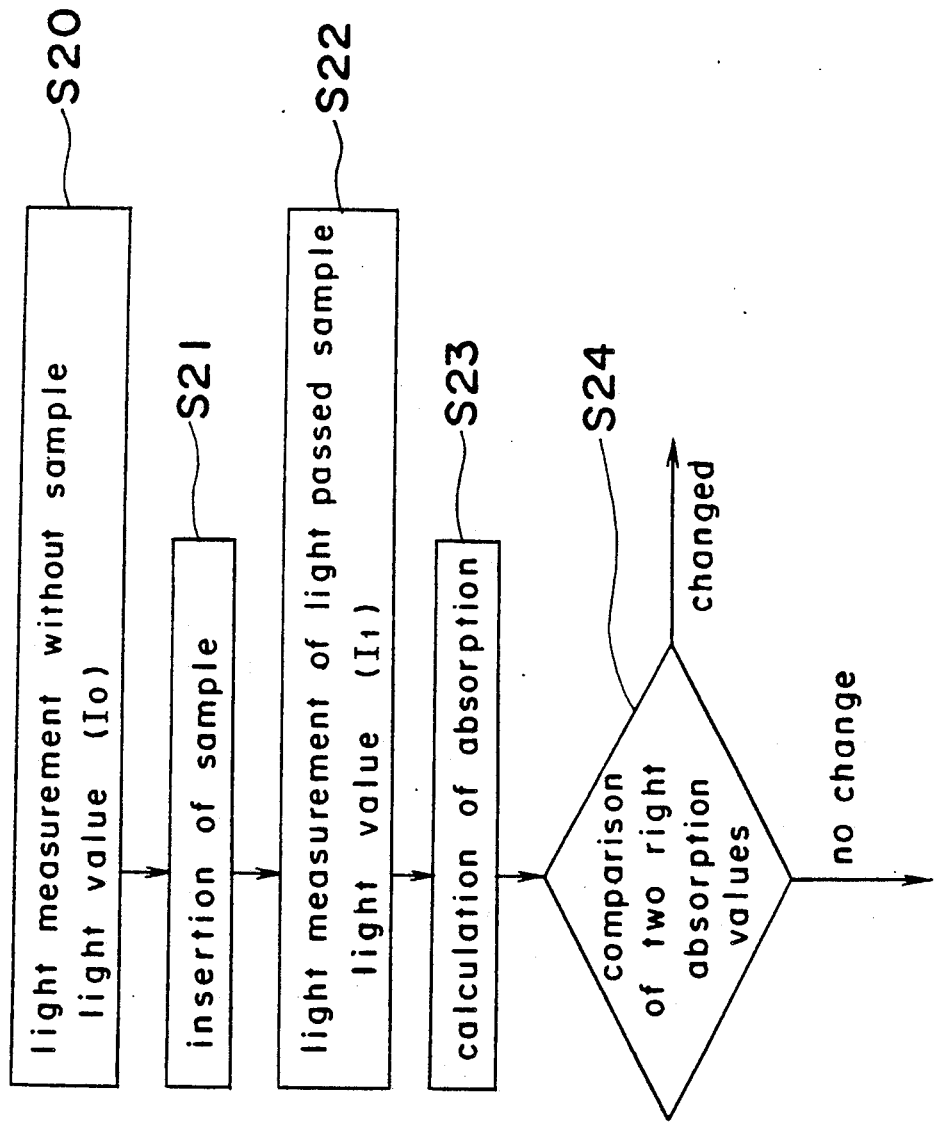

In order to calculate the change of the light absorption, the computer 6 performs the processing as shown in FIG. 5 based on the light value signal obtained by the photo transistor 7 and converted in a digital form by the A/D converter 8.

Referring to FIG. 5, in the step S20, the computer takes the incident light value $I_0$ when no sample is present in the well 1. After the sample is inserted in the well 1 in the step S21, the computer 6 takes, from the output of the A/D converter 8, the light value $I_1$ which is the amount of the light passing the sample in the well 1. Then the light absorption is calculated in the step S23 based on the equation "$-\log I_1/I_0$". The measurement and calculation are repeated every predetermined period. The calculated light absorption obtained in the present period is compared with the light absorption calculated in the last period in the past in the step S24 so as to detect whether or not a change of the light absorption occurs.

In case the number of the living cells calculated in the step S6 is smaller than a predetermined value and the change of the light absorption is larger than a further predetermined value, the computer 6 judges that there are undesired organisms in the well.

The details of the process of the counting of the living cells are disclosed in the PCT/JP 87/00750 and the disclosure thereof is cited as the reference.

The matching process for taking out the living cells may be made by known manner but there may be used a matching filter arrangement in the form of a hardware.

EXAMPLES

Myeloma cells Sp2/O contained in DULBECCO MEM culture solution with $10^3$/ml were poured in every well of a 96 well microplate and were cultured in a $CO_2$ incubator for a day. Subsequently the microplate was taken out of the $CO_2$ incubator and the number of cultured living cells and the light absorption change were measured.

The number of cultured living cells were counted in such a manner that image signals obtained by a CCD camera 3 coupled to a microscope 2 for observing the cells in a well 1 were input into an image signal processor 5 (PIAS-1 manufactured by Nippon PC Systems) and were digitized. The image obtained by the CCD camera 3 were also input in a monitor television receiver 4.

Magnification was such that, as shown in FIG. 2, the contours or outline of one cell correspond to the peripheral edges of a spatial filter made of $7 \times 7$ matrix of the pixels. The size of the single pixel was 1.8 $\mu$m $\times$ 1.8 $\mu$m. The image signals obtained by the CCD camera were digitized with 64 gradation gray scales. The pattern of the spatial filter for the matching was set as shown in FIG. 2. In FIG. 2, 0 shows the pixel area in which the image of the cell is not present and 1 shows the pixel area in which the brightness of the living cell is high and −1 shows the picture element area in which the brightness of the living cell is low.

After the image signals were converted into a binary digitized form, the number of the living cells were measured by a computer 6 according to an equation (1).

$$N = N_p/N_x \quad (1)$$

wherein
N is the number of the living cells
$N_p$ is the number of pixels in which the living cells are present and
Nx is the number of the picture elements occupied by single cell.

In order to measure the change of the light absorption, as the test agent, phenol red (phenolsulphophtalein) was used with such a low concentration that it did not harm the living cells. The light absorption was measured with respect to either the lights of 430 nm and 558 nm wave lengths at which light absorption peaks occurred and the light of 650 nm wave length at which the absorption by the phenol red did not occur. Then pH value was calculated using the equation 2.

$$pH = 1.2 \log \frac{Abs558 - Abs650}{Abs430 - Abs650} + 7.6 \quad (2)$$

wherein Abs558, Abs650 and Abs430 are the light absorption of 558 nm, 650 nm and 430 nm wave lights.

pH was calculated according to the linear relation shown in FIG. 3.

After the measurements of the number of the living cells, the light absorption of the 650 nm wave length and pH value, the micro plate containing the living cells was put in air for one day. Then the micro plate was taken in the incubator to culture for one day. Subsequently, the number of the living cells, light absorption of the light of 650 nm wave length and pH were again measured.

The result of the measurement are shown in the table 1.

TABLE 1

| | before putting in the air | | | after putting in the air | | |
|---|---|---|---|---|---|---|
| well NO. | number of living cells N/mm² | Abs650 | pH | number of living cells N/mm² | Abs650 | pH |
| 1 | 20 | 0.0319 | 7.4 | 75 | 0.0327 | 7.4 |
| 2 | 27 | 0.0348 | 7.4 | 36 | 0.153 | 7.4 |
| 3 | 24 | 0.0384 | 7.4 | 48 | 0.102 | 7.1 |

By the observation of the wells by a microscope, the living cells were observed only in the No. 1 well. In the No. 2 well, the number of the cultured living cells was small and the visible light absorption was largely increased and it was recognized that undesired microorganisms grew. In the No. 3 well, in which the number of the cultured living cells was small and pH calculated from the change of the visible light absorption was greatly decreased, it was recognized that the gram negative aerobic bacilli grew. By these results, it is apparent that contaminant by the undesired microorganisms can be detected by the method according to the present invention.

As apparent from the foregoing, according to the present invention, it is possible to detect the presence of the undesired microorganisms in the culture solution by the change of the visible light absorption and the number of the cultured living cells which is obtained by the digital cultured cell image taken in the image processor through the television camera coupled to the observation means such as microscope when the cells grow in a container which allows passage of visible light. According to the method of the present invention, since the invasion by the undesired microorganisms can be automatically detected in a short period without contacting, invasion of the undesired microorganisms can be decreased. It is possible to decrease the bad effect of the undesired microorganisms to the desired organisms by shortening the period of time during which the cells are out of the culturing atmosphere. In particular, it is advantageous that when a large number of cell containers must be controlled, the invasion of the undesired microorganisms can be easily detected with a high accuracy in a short period.

What is claimed is:

1. A method for detecting undesired microorganisms in a cell culture in a light permeable container of which digital pictures have been obtained by a picture processing device from a signal from a television camera coupled to an observation means, comprising the steps of:
   counting the number of cultured living cells appearing in a picture;
   measuring the change of absorption of the visible light by the cultured solution; and
   signaling the presence of unwanted organisms when the number of the cultured living cells is small and the visible light absorption is greatly increased compared to the light absorption at a most recent previous measurement.

2. The method according to claim 1 wherein, the visible light is light that is not absorbed by an indicator contained in the culture solution.

3. The method according to claim 1 further comprising the step of:
   signaling the presence of unwanted organisms when the number of the cultured living cells is small and a measured pH value of the culture solution is greatly decreased compared to a most recent previously measured pH value.

4. The method according to claim 3 wherein the pH values are calculated from the change of the visible light absorption in the culture solution.

5. The method according to claim 4, wherein the change of absorption of visible light is the change of absorption of more than two kinds of light, one of which is absorbed by an indicator contained in the culture solution and another of which is not absorbed by the indicator.

6. The method according to claim 4, wherein the change of the visible light absorption includes more than two kinds of change, and at least one kind of change is caused by absorption by phenol red contained in the culture solution.

7. A method for detecting undesired microorganisms in a cell culture in a light permeable container comprising the steps of:
   counting the number of living cells in the culture;
   measuring the absorption of visible light by the cultured solution; and
   signaling the presence of unwanted organisms when the number of the cultured living cells is small and a measured pH value of the culture solution is greatly decreased compared to a most recent previously measured pH value.

8. The method according to claim 7 wherein the pH values are calculated from the change of the visible light absorption in the culture solution.

9. The method according to claim 8, wherein the change of absorption of visible light is the change of absorption of more than two kinds of light, one of which is absorbed by an indicator contained in the culture solution and another of which is not absorbed by the indicator.

10. The method according to claim 8, wherein the change of the visible light absorption includes more than two kinds of change, and at least one kind of change is caused by absorption by phenol red contained in the culture solution.

* * * * *